(12) United States Patent
Gammans (10) Patent No.: US 11,020,354 B2
(45) Date of Patent: Jun. 1, 2021

(54) FORMULATIONS OF N-ACETYLCYSTEINE AND USES THEREOF

(71) Applicant: Otologic Pharmaceutics, Inc., Oklahoma City, OK (US)

(72) Inventor: Richard E. Gammans, Edmond, OK (US)

(73) Assignee: Otologic Pharmaceuticals, Inc., Oklahoma City, OK (US)

(*) Notice: Subject to any disclaimer, the term of this patent is extended or adjusted under 35 U.S.C. 154(b) by 0 days.

(21) Appl. No.: 15/874,285

(22) Filed: Jan. 18, 2018

(65) Prior Publication Data

US 2018/0200192 A1    Jul. 19, 2018

Related U.S. Application Data (60) Provisional application No. 62/448,362, filed on Jan. 19, 2017.

(51) Int. Cl.
| | |
|---|---|
| *A61K 9/48* | (2006.01) |
| *A61K 31/19* | (2006.01) |
| *A61K 31/185* | (2006.01) |
| *A61P 25/00* | (2006.01) |
| *A61P 27/16* | (2006.01) |
| *A61P 13/12* | (2006.01) |
| *A61P 1/16* | (2006.01) |

(52) U.S. Cl.
CPC .......... *A61K 9/4891* (2013.01); *A61K 9/4808* (2013.01); *A61K 31/185* (2013.01); *A61K 31/19* (2013.01); *A61P 1/16* (2018.01); *A61P 13/12* (2018.01); *A61P 25/00* (2018.01); *A61P 27/16* (2018.01)

(58) Field of Classification Search
None
See application file for complete search history.

(56) References Cited

U.S. PATENT DOCUMENTS

| | | |
|---|---|---|
| 5,488,145 A | 1/1996 | Carney |
| 2012/0093939 A1 | 4/2012 | Payne et al. |
| 2012/0157534 A1 | 6/2012 | Harty |
| 2012/0172435 A1 | 7/2012 | Kopke et al. |
| 2014/0030323 A1 | 1/2014 | Arad et al. |
| 2014/0322315 A1 | 10/2014 | Dohil et al. |
| 2016/0158173 A1 | 6/2016 | Kopke et al. |

FOREIGN PATENT DOCUMENTS

| | | |
|---|---|---|
| WO | WO 2008/013866 A2 | 1/2008 |
| WO | WO 2011/028503 A1 | 3/2011 |
| WO | WO 2013/171270 A1 | 11/2013 |

OTHER PUBLICATIONS

Eudragit® Brochure—Evonik Industries, Dec. 15, 2012, pp. 1-16—date provided on Google Search History (Year: 2012).*

(Continued)

*Primary Examiner* — Aradhana Sasan
(74) *Attorney, Agent, or Firm* — Foley & Lardner LLP (57) ABSTRACT

Disclosed herein are compositions comprising a first compound that is N-acetylcysteine or a salt thereof, optionally a second compound that is a pharmaceutically acceptable compound capable of forming a radical adduct; and a coating layer encapsulating at least the first compound. Also disclosed are methods of use and manufacture.

19 Claims, 4 Drawing Sheets

(56) References Cited

OTHER PUBLICATIONS

Fetoni, "Protective effects of N-acetylcysteine on noise induced hearing loss in guinea pigs," *ACTA Ortorhinoloaryngologica Italica*, vol. 29, pp. 70-75 (2009).

Bogström, et al., "Pharmacokinetics of N-Acetylcystein in Man," *Eureopean Journal of Clinical Pharmacology*, vol. 31, pp. 217-222 (1986).

Kopke, et al., "Reduction of noise-induced hearing loss using L-NAC and salicylate in the chinchilla," vol. 149, pp. 138-146 (Jul. 2000).

Lin, et al., "N-Acetyl-cysteine against noise-induced temporary threshold shift in male workers," *Hearing Research*, vol. 269, p. 42-47 (2010).

Lorito et al., "Different strategies in treating noiseinduced hearing loss with N-acetylcystein," *Med. Sci. Monit.*, vol. 14, No. 8, pp. 159-164 (2008).

Mortazavi, et al., "Effects of N-Acetylcystein on Auditory Brainstem Response Threshold Shift in Rabbits Exposed to Noise and Carbon Monoxide," *American Journal of Applied Sciences*, vol. 7, No. 2, pp. 201-207 (2010).

Lindblad, et al., "The efficacy of N-Acetylcystein to protect the human cochlea from subclinical hearing loss caused by impulse noise: A controlled trial," *Noise& Health*, vol. 13, No. 55, pp. 392-401 (2011).

International Search Report and Written Opinion issued in related International Patent Application No. PCT/US2018/014183, dated May 10, 2018.

International Preliminary Report on Patentability issued in related International Patent Application No. PCT/US2018/014183, dated Aug. 1, 2019.

Search Report issued in co-pending European Patent Application No. 18741521.1, dated Aug. 24, 2020.

\* cited by examiner

FORMULATIONS OF N-ACETYLCYSTEINE AND USES THEREOF

CROSS REFERENCE TO RELATED APPLICATIONS

This application claims priority to U.S. Provisional Application No. 62/448,362 filed Jan. 19, 2017, which is incorporated herein by reference in its entirety.

BACKGROUND

N-acetylcysteine ("NAC") is a thiol-containing amino acid derivative that acts as a radical oxygen species ("ROS") scavenger and a substrate for glutathione ("GSH"), the major endogenous antioxidant produced by cells. NAC has been shown to reduce noise induced hearing loss (NIHL) in animal models (Fetoni 2009; Kopke 2000; Lorito 2008; Mortazavi 2010) and correlates of noise-induced cochlear injury in clinical trials (Lin 2010; Lindblad 2011) (Kopke, submitted).

While NAC has shown promising results, it suffers from low bioavailability and/or short terminal half-life. The current uses of NAC, therefore, have required high dosing regimens or constant administration. Studies, however, have shown that releasing NAC from a slow-release formulation reduces the oral availability of NAC. Bogström, L., et al., Eur J Clin Pharmacol (1986) 31: 217).

Therefore, a need exists for innovative formulations that can provide convenient dosage forms of NAC and, in turn, increase its bioavailability and/or terminal half-life. Such an advance would reduce dosage amount, reduce dosage periodicity, and/or increase therapeutic effect.

SUMMARY

The disclosure relates to modified release solid dosage forms comprising a first compound that is N-acetylcysteine ("NAC") or a salt thereof; optionally a second compound that is a pharmaceutically acceptable compound capable of forming a radical adduct; and a coating layer encapsulating at least the first compound.

While Rather than observing a reduction in systemic absorption of NAC, as predicted by the published literature (e.g., Borgström, L., et al.), Applicant unexpectedly discovered that the opposite effect (i.e., greater systemic absorption) is actually observed.

Accordingly, some aspects of the present disclosure include a modified release dosage form comprising (a) a first compound that is N-acetylcysteine or a salt thereof; (b) optionally, a second compound that is a pharmaceutically acceptable compound capable of forming a radical adduct; and (c) a coating layer encapsulating the first compound, wherein the coating layer solubilizes in the mammal's duodenum and prevents release of the first compound in a gastrointestinal tract before a mammal's duodenum upon oral administration, or wherein the coating layer solubilizes at a pH of greater than 5.4 in a physiological environment.

In some embodiments, the second compound comprises a nitrone moiety. In some embodiments, the second compound is 2,4-disulfophenyl-N-tert-butyl nitrone, or a salt thereof. In some embodiments, the second compound is disodium 2,4-disulfophenyl-N-tert-butyl nitrone, 4-hydroxyphenyl-N-tert-butyl nitronr, phenyl-N-tert-butyl nitrone, or pharmaceutically acceptable salts thereof. In some embodiments, the coating layer encapsulates the first compound and the second compound. In some embodiments, the coating layer solubilizes at a pH of greater than 7.0 in a physiological environment. In some embodiments, the weight ratio of the N-acetylcysteine to the pharmaceutically acceptable compound capable of forming a radical adduct is from about 1:0.08 to about 1:8. In some embodiments, the molar ratio of about 1:0.03 to about 1:35. In some embodiments, the composition is in the form of a tablet or capsule. In some embodiments, the composition is in the form of a capsule comprising coated pellets or beads. In some embodiments, the composition is a pharmaceutical composition suitable for oral administration.

Additional aspects of the present disclosure include a modified release pharmaceutical composition comprising pellets or beads comprising N-acetylcysteine or a salt thereof, and optionally a second compound that is a pharmaceutically acceptable compound capable of forming a radical adduct, wherein the pellets or beads comprise a core that comprises N-acetylcysteine or a salt thereof and a coating encapsulating the core that prevents release of the first compound at a pH of less than 5.5.

In some embodiments, the second compound is in the form of pellets, and the pellets comprise a core that contains the second compound and a coating encapsulating the core that prevents release of the second compound at a pH of less than 5.5. In some embodiments, the second compound is a 2,4-disulfophenyl-N-tert-butyl nitrone, or a salt thereof. In some embodiments, the second compound is the pharmaceutically acceptable salt, disodium 2,4-disulfophenyl-N-tert-butyl nitrone. In some embodiments, the modified release pharmaceutical composition is in the form of a capsule. In some embodiments, the coating for the pellets comprising N-acetylcysteine or a salt thereof and the coating for the pellets comprising the second compound are of the same composition. In some embodiments, the pellets comprising N-acetylcysteine or a salt thereof also comprise the second compound. In some embodiments, the pharmaceutical composition, after a single administration to a human subject in need of treatment thereof, produces in the subject a mean area under the curve (0-inf) ($AUC_{0-inf}$) of N-acetylcysteine that is greater than administration of a pharmaceutical composition containing an equivalent composition of N-acetylcysteine or a salt thereof, but without a coating encapsulating a core that prevents release of the first compound at a pH of less than 5.5. In some embodiments, the weight ratio of the N-acetylcysteine to the pharmaceutically acceptable compound capable of forming a radical adduct is from about 1:0.08 to about 1:8. In some embodiments, the coating layer provides for release of the N-acetylcysteine or a salt thereof within a mammal's duodenum upon oral administration.

Additional aspects of the present disclosure include a method of treating acute acoustic trauma, sensory neural hearing loss, tinnitus, vertigo, Meniere's disease, aminoglycoside, carboplatin, or cisplatin induced hearing loss, endolymphatic hydrops, stroke, or renal or hepatic damage in a subject in need thereof comprising administering an enteric-coated N-acetylcysteine or a salt thereof and one or more compounds that is a pharmaceutically acceptable compound capable of forming a radical adduct.

In some embodiments, the pharmaceutically acceptable compound capable of forming a radical adduct is 2,4-disulfophenyl-N-tert-butyl nitrone, or a pharmaceutically acceptable salt thereof. In some embodiments, the enteric-coated N-acetylcysteine or a salt thereof and the pharmaceutically acceptable compound capable of forming a radical adduct are co-administered. In some embodiments, the enteric-coated N-acetylcysteine or a salt thereof and the pharmaceutically acceptable compound capable of forming a radical adduct are each administered orally. In some embodiments, the method is a method of treating acute acoustic trauma. In some embodiments, the enteric-coated N-acetylcysteine or a salt thereof and the pharmaceutically acceptable compound capable of forming a radical adduct are administered within from about 0.5 to about 48 hours after the acute acoustic trauma. In some embodiments, the N-acetylcysteine or a salt thereof is administered in an amount of from about 300 mg to about 2400 mg, based on the weight of N-acetylcysteine moiety. In some embodiments, the N-acetylcysteine or a salt thereof is administered in an amount as disclosed elsewhere in this description. In some embodiments, the amount of pharmaceutically acceptable compound capable of forming a radical adduct is administered in an amount of from about 250 mg to about 3000 mg, based on the weight of pharmaceutically acceptable compound capable of forming a radical adduct moiety. In some embodiments, the amount of pharmaceutically acceptable compound capable of forming a radical adduct is administered in an amount as disclosed elsewhere in this description. In some embodiments, the subject in need thereof is a mammal. In some embodiments, the mammal is a human.

Additional aspects of the present disclosure include a method of increasing systemic exposure of N-acetylcysteine in a mammal comprising orally administering a composition comprising (a) N-acetylcysteine or a salt thereof in a core of the composition and (b) a gastro-resistant coating layer that encapsulates the core and provides for release of the N-acetylcysteine or a salt thereof in the mammal's duodenum, wherein after a single administration to the mammal the systemic exposure of N-acetylcysteine is greater than the systemic exposure of an equivalent N-acetylcysteine composition that lacks the gastro-resistant coating layer.

In some embodiments, the composition comprising N-acetylcysteine or a salt thereof and a coating layer is in the form of pellets or beads. In some embodiments, the coating layer that begins to solubilize at a pH of greater than 6.8 in a physiological environment. In some embodiments, the systemic exposure is quantified by a mean area under the curve (0-inf) ($AUC_{0-inf}$) of N-acetylcysteine. In some embodiments, the N-acetylcysteine or a salt thereof is administered in an amount of from about 300 mg to about 2400 mg, based on the weight of N-acetylcysteine moiety. In some embodiments, the pellets have a mean diameter of about 0.5 mm to about 2.8 mm. In some embodiments, the gastro-resistant coating layer comprises Pharmacoat 606, USP Hypromellose or EUDRAGIT L 30 D-55. In some embodiments, the N-acetylcysteine or a salt thereof is c-administered with another active agent. In some embodiments, the mammal is a human.

These and other features, together with the organization and manner of operation thereof, will become apparent from the following detailed description when taken in conjunction with the accompanying drawings.

DETAILED DESCRIPTION

The disclosure relates to modified release solid dosage forms comprising a first compound that is N-acetylcysteine ("NAC") or a salt thereof; optionally a second compound that is a pharmaceutically acceptable compound capable of forming a radical adduct; and a coating layer encapsulating at least the first compound.

The modified release dosage forms of the present disclosure can achieve any one of a number of objects. First, the modified release dosage forms of the present disclosure, when administered to a subject in need of treatment thereof, provide a systemic exposure of NAC or a salt or metabolite thereof that is significantly increased as compared to a similar immediate release dosage form of NAC, as determined, e.g., by AUC values. Second, because the dosage forms of the present disclosure provide for an increased systemic exposure of NAC or a salt or metabolite thereof, these solid dosage forms can be used to treat a variety of different conditions or diseases, such as, but not limited to, acute acoustic trauma, sensory neural hearing loss, tinnitus, vertigo, or endolympahtic hydrops, Meniere's disease, ototoxin induced hearing loss e.g. aminoglycoside, ototoxin-induced injury, acetaminophen (Tylenol) poisoning, collapse of part or all of a lung (atelectasis), chest pain (angina), bipolar disorder, Air passage swelling (bronchitis), chronic obstructive pulmonary disease (COPD), fibrosing alveolitis, diagnostic lung tests, or stroke.

First Compound: NAC or a Pharmaceutically Acceptable Salt Thereof

The first compound in the modified release dosage forms of the present disclosure is NAC or a pharmaceutically acceptable salt thereof. In some embodiments, the NAC is an isomerically pure or enriched (e.g., 95, 96, 97, 98, 99, 99.5, 99.9 e.e.) form of N-acetyl-L-cysteine. In some embodiments, the NAC is a racemic mixture of N-acetylcysteine.

In some embodiments, the modified release dosage form comprises a plurality of pellets of NAC or the pharmaceutically acceptable salt thereof. The pellets may be, for example a target size 0.5 mm up to a target size of 2.5 mm±10% with no pellets over that 2.8 mm.

The NAC or a pharmaceutically acceptable salt thereof may be present in the modified release dosage form in a pharmaceutically acceptable amount, or a portion thereof, for example 50% of a pharmaceutically acceptable amount when the modified release dosage form is intended to be dosed at two capsules or tablets (e.g., compressed tablets). For example, in some embodiments, the NAC or pharmaceutically acceptable salt thereof is contained in the modified release dosage form in an amount of from about 300 mg to about 2400 mg. For example, some embodiments include about 300, 400, 500, 600, 700, 800, 900, 1000, 1100, 1200, 1300, 1400, 1500, 1600, 1700, 1800, 1900, 2000, 2100, 2200, 2300, or 2400, and values or ranges therein between mg NAC. In some embodiments, this weight of NAC or pharmaceutically acceptable salt thereof is based on the weight of N-acetylcysteine moiety so that the counter-ion of a pharmaceutically acceptable salt does not affect the molar amount of NAC.

Second Compound: A Pharmaceutically Acceptable Compound Capable of Forming a Radical Adduct The second compound in the modified release dosage forms of the present disclosure is a pharmaceutically acceptable compound capable of forming a radical adduct. The second compound is optional, and in some embodiments, is not present.

In some embodiments, the compound comprises a nitrone moiety. For example, in some embodiments, the compounds capable of forming a radical adduct is selected from the group consisting of alpha-phenyl-N-tert-butyl nitrone, 2-sulfophenyl-N-tert-butyl nitrone, 2,4-disulfophenyl-N-tert-butyl nitrone, and pharmaceutically acceptable salts thereof. In some embodiments, the nitrone compound is selected from phenyl butyl nitrone (PBN) and its derivatives. In some embodiments, the nitrone compound is PBN. In some embodiments, the nitrone compound is 4-hydroxy-α-phenyl butyl nitrone (4-OHPBN). In some embodiments, the nitrone compound is 2-sulfonyl-α-phenyl tertiary butyl nitrone (S-PBN).

In a preferred embodiment, the second compound is 2,4-disulfophenyl-N-tert-butyl nitrone, or pharmaceutically acceptable salts thereof, e.g., disodium 2,4-disulfophenyl-N-tert-butyl nitrone, dipotassium 2,4-disulfophenyl-N-tert-butyl nitrone, and the like.

The 2,4-disulfonyl α-phenyl tertiary butyl nitrone is also referred to as 2,4-disulfonyl PBN, 2,4-DSPBN, NXY-059 or HPN-07. The disodium salt of 2,4-DSPBN has the following structure:

The acid form of 2,4-DSPBN has the following structure:

The acid form may be a solid or found in low pH solutions. The ionized salt form of the compound exists at higher pH and may be represented by either of the following structures:

In the salt form, X is a pharmaceutically acceptable cation. Most commonly, this cation is a monovalent material such as sodium, potassium or ammonium, but it can also be a multivalent alone or cation in combination with a pharmaceutically acceptable monovalent anion, for example calcium with a chloride, bromide, iodide, hydroxyl, nitrate, sulfonate, acetate, tartrate, oxalate, succinate, pamoate or the like anion; magnesium with such anions; zinc with such anions or the like. Among these materials, the free acid and the simple sodium, potassium or ammonium salts are most preferred with the calcium and magnesium salts also being preferred but somewhat less so. 2,4-DSPBN is described in detail by U.S. Pat. No. 5,488,145, which is incorporated herein by reference. The salts of 2,4-DSPBN may also be used for facilitating the transport of therapeutic or diagnostic agents across the BBB or the BCB or the BCSFB in a manner similar to the use of 2,4-DSPBN as described herein.

The 2,4-DSPBN or pharmaceutically acceptable salt thereof may be present in the modified release dosage form in a pharmaceutically acceptable amount, or a portion thereof, for example 50% of a pharmaceutically acceptable amount when the modified release dosage form is intended to be dosed at two capsules. For example, in some embodiments, the 2,4-DSPBN or pharmaceutically acceptable salt thereof is contained in the modified release dosage form in an amount of from about 250 mg to about 3000 mg. For example, some embodiments include about 250, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900 or 3000 mg, and values or ranges therein between, 2,4-DSPBN or pharmaceutically acceptable salt. In some embodiments, this weight of 2,4-DSPBN or pharmaceutically acceptable salt thereof is based on the weight of 2,4-DSPBN moiety so that the counter-ion of a pharmaceutically acceptable salt does not affect the molar amount of 2,4-DSPBN.

Coating Layer

The coating layer of the modified release dosage forms of the present disclosure provides for delayed or modified delivery of the first and/or second compound.

In some embodiments, the coating layer prevents release of the first compound before a mammal's duodenum upon oral administration. In other embodiments, the coating layer solubilizes at a pH of greater than 5.4 or 5.5 in a physiological environment. In some embodiments, the coating layer solubilizes at a pH of greater than about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1 or 7.2, and values or ranges therein between in a physiological environment In other embodiments, the coating layer prevents release of the first compound at a pH of less than 5.5 in a physiological environment. In some embodiments, the coating layer prevents release of the first compound at a pH of less than about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1 or 7.2, and values or ranges therein between in a physiological environment. The physiological environment may be replicated, for example, by following the requirements of the United States Pharmacopeia (USP) disintegration test for enteric coated tablets.

The amount of coating material required in the preparations will depend on the dissolution properties of the particular coating material and the planned dosage form in mind. Usually the amount of coating material will be up to 25% (dry weight gain). The coating may be applied from solvent based solutions or aqueous dispersions. Suitable solvents are for example different alcohols, such as isopropanol and ethanol, and acetone or their mixtures. The solvent based solutions may also contain water, usually at most one equivalent, and the aqueous dispersions may contain water miscible organic solvents. The coating may contain additives, such as coloring agents, plasticizers, such as alkylphthalates (e.g. dibutylphthalate), polyethylene glycol, triacetin, citric acid esters and propylene glycol, auxiliary materials, e.g. talc, etc.

In some embodiments, the coating material comprises a delayed release enteric polymers. Suitable examples of delayed release enteric polymers include, but are not limited to cellulose acetate phthalate, cellulose acetate trimellitate, hydroxypropyl methylcellulose phthalate, polyvinyl acetate phthalate, carboxymethylethylcellulose, co-polymerized methacrylic acid/methacrylic acid methyl esters such as, for instance, materials known under the trade name EUDRAGIT® L12.5, L100, EUDRAGIT® S12.5, S100, or similar compounds used to obtain enteric coatings. Co-polymerized methacrylic acid/methacrylic acid methyl esters generally comprise three subclasses of compound: methacrylic acid copolymer type A, methacrylic acid copolymer type B, and methacrylic acid copolymer type C. The various types of copolymers represent compounds with varying ratios of methacrylic acid to methacrylic acid methyl ester. Accordingly, methacrylic acid copolymer type A has a ratio of methacrylic acid to methacrylic acid methyl ester of approximately 1:1, type B has a ratio of approximately 1:2, and type C has a ratio similar to type A, but may incorporate additional components, such as surfactants. Aqueous colloidal polymer dispersions or re-dispersions can be also applied, including, for example, the polymers sold under the trade name EUDRAGIT® L 30D-55, EUDRAGIT® L100-55, EUDRAGIT® S100, EUDRAGIT® preparation 4110D (Rohm Pharma); EUDAGRITO FS 30D; AQUATERIC®, AQUACOAT® CPD 30 (FMC); KOLLICOAT MAE® 30D and 30DP (BASF); and EASTACRYL® 30D (Eastman Chemical). In one aspect, the delayed release enteric polymer comprises methacrylic acid copolymer type A. In still yet another aspect, the delayed release enteric polymer comprises a mixture of methacrylic acid copolymer type A and methacrylic acid copolymer type B.

One skilled in the art will appreciate that additional components may be added to the delayed release polymers without departing from the scope of the disclosure. For instance, a plasticizer may be added to the delayed release enteric polymers to improve the physical characteristics of the delayed release polymeric layer. Non-limiting examples of plasticizers include triethyl citrate, acetyl triethyl citrate, tributyl citrate, acetyl tributyl citrate, trihexyl citrate, acetyl trihexyl citrate, trioctyl citrate, acetyl trioctyl citrate, butyryl trihexyl citrate, acetyl butyryl trihexyl citrate, trimethyl citrate, acetylated monoglycerides, and alkyl sulphonic acid phenyl esters. In yet another aspect, the plasticizer comprises triethyl citrate.

Furthermore, the enteric polymers used in this disclosure can be modified by mixing with other known coating products that are not pH sensitive. Examples of such coating products include the neutral methacrylic acid esters with a small portion of trimethylammonioethyl methacrylate chloride, sold currently under the trade names EUDRAGIT® and EUDRAGIT® RL; a neutral ester dispersion without any functional groups, sold under the trade names EUDRAGIT® NE30D and EUDRAGIT® NE30; and other pH independent coating products.

It is also within the scope of this disclosure that an additional modifying layer may be added on top of the enteric coating layer. This modifying layer can include a water penetration barrier layer (semipermeable polymer) which can be successively coated after the enteric coating to reduce the water penetration rate through the enteric coating layer and thus increase the lag time of the drug release. Controlled-release coatings commonly known to one skilled in the art can be used for this purpose by conventional coating techniques such as pan coating or fluid bed coating using solutions of polymers in water or suitable organic solvents or by using aqueous polymer dispersions. For example, the following non-limiting list of controlled release polymers may be used in the current disclosure: cellulose acetate, cellulose acetate butyrate, cellulose acetate propionate, ethylcellulose, hydroxypropyl methylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(ethylene), poly(ethylene) low density, poly(ethylene) high density, poly(propylene), poly(ethylene oxide), poly(ethylene terephthalate), poly(vinyl isobutyl ether), poly(vinyl acetate), poly(vinyl chloride), polyurethane, ethylcellulose aqueous dispersions such as AQUACOAT® and SURELEASE®, poly(butyl methacrylate, (2-dimethylaminoethyl) methacrylate, methyl methacrylate), poly(methacrylic acid, methyl methacrylate), poly(methacrylic acid, ethylacrylate), poly(methyl acrylate, methyl methacrylate, methacrylic acid), poly(ethylacrylate, methylmethacrylate, trimethylammonioethyl methacrylate chloride), poly(ethylacrylate, methyl methacrylate), poly(methacrylic acid, ethylacrylate), type A methacrylic acid copolymer, type B methacrylic acid copolymer, type C methacrylic acid copolymer, methacrylic acid copolymer dispersion, aqueous acrylic polymer dispersion, (EUDRAGIT® compounds), OPADRY®, fatty acids and their esters, waxes, zein, and aqueous polymer dispersions such as EUDRAGIT® RS and RL 30D, EUDRAGIT® NE 30D, cellulose acetate latex. The combination of above polymers and hydrophilic polymers such as hydroxyethyl cellulose, hydroxypropyl cellulose (KLUCEL®, Hercules Corp.), hydroxypropyl methylcellulose (METHOCEL®, Dow Chemical Corp.), and polyvinylpyrrolidone may also be incorporated. In one aspect, the controlled release polymer comprises ethylcellulose, hydroxypropyl methylcellulose, and combinations thereof. In yet another aspect, the controlled release polymer comprises a combination of ethylcellulose and hydroxypropyl methylcellulose in a ratio of ethylcellulose to hydroxypropyl methylcellulose ranging from about 0.1 to about 10, from about 0.2 to about 5, from about 0.5 to about 3, and from about 1 to about 2. In still yet another aspect, the controlled release polymer comprises a combination of ethylcellulose aqueous dispersion and hydroxypropyl methylcellulose in a ratio of ethylcellulose aqueous dispersion to hydroxypropyl methylcellulose ranging from about 0.1 to about 10, from about 0.1 to about 5, from about 0.5 to about 4, and from about 1.5 to about 3.

The coating to the preparations may be achieved by conventional coating techniques as defined above, such as by the use of spraying, fluidized bed, immersion tube and immersion bed techniques.

In some embodiments, the coating layer is formulated to release the first and/or second compound in the within a mammal's (e.g., adult human's) duodenum upon oral administration.

Modified Release Dosage Form Compositions

The modified release dosage forms of the present disclosure comprise a first compound and optionally a second compound. When both first and second compound are present, the weight ratio of the N-acetylcysteine to the radical adduct is from about 1:0.08 to about 1:8. For example, the weight ratio may be about 1 to about 0.08, 0.09, 0.1, 0.15, 0.2, 0.25, 0.3, 0.4, 0.5, 0.6, 0.7, 0.8, 0.9, 1.0, 2, 3, 4, 5, 6, 7 or 8, and values or ranges therein between.

The modified release dosage forms of the present disclosure may be in the form of a solid oral medicament. For example, in some embodiments, the modified release dosage form is selected from a tablet or capsule. The first compound and optionally a second compound may be in the form of pellets or beads within a capsule, for example.

In embodiments where the first or second compound is in the form of beads, the first or second compound layered on an inert core such as sugar spheres or microcrystalline cellulose spheres by means of a suitable polymeric binder. The polymeric binder functions to create a sealcoat around the inert core material, improving the friability of the inert core. The polymeric binder may comprise any of the immediate release polymers previously described. In one aspect, the polymeric binder comprises hydroxypropyl methylcellulose. The beads may then be coated by one or more layers, including the coating layer described herein.

One skilled in the art will appreciate that the various modified release beads of the current disclosure may be manufactured by any means known in the art. Examples of non-limiting methods of manufacturing the beads include fluid bed processing, centrifugal granulation, extrusion-spheronization, high shear granulation, melt extrusion, and solution or suspension layering. In a fluid bed process, the immediate release polymer is dissolved in water and micronized drug is suspended in the immediate release polymer solution. This suspension is then sprayed onto inert spherical support beads such as sugar spheres or microcrystalline cellulose spheres. Alternately, non-micronized drug can be suspended in the immediate release polymer solution and the suspension can be passed through a mill. In the centrifugal granulation process, the inert beads are placed in the granulator on a rotating disc at the bottom of the granulator. Micronized drug is introduced into the granulator and a solution of the immediate release polymer is sprayed at the same time. Extrusion and spheronization is another manufacturing method for immediate release beads, wherein the drug is mixed with dry excipients and wet-massed by addition of a binder solution and extruded to form spaghetti-like strands. The extrudate is then chopped and converted to dense spherical beads using a spheronizer. Another method of producing beads includes high shear granulation. High shear granulation involves dry mixing the active component and other components. Then the mixture is wetted by addition of a binder solution in a high shear-granulator/mixer. The granules are kneaded after wetting by the combined action of mixing and milling. The resulting granules or pellets are subsequently dried and sieved. An additional method comprises melt-extrusion or melt-granulation. This process generally involves melting a normally solid hydrophobic binder material, e.g. a wax or similar substance, and incorporating a powdered drug therein. To obtain a controlled or extended release dosage form, additional hydrophobic release materials, e.g. ethylcellulose or a water-insoluble acrylic polymer, may be incorporated into the molten wax hydrophobic binder material. Further, solution or suspension layering involves a process whereby an active component solution or dispersion with or without a binder is sprayed onto starting seeds with a certain particle size in a fluidized bed processor or other suitable equipment. The drug thus is coated on the surface of the starting seeds. The drug-loaded pellets are dried for further applications.

In some embodiments, the modified release dosage form comprises a plurality of pellets of 2,4-DSPBN or the pharmaceutically acceptable salt thereof. The pellets may be, for example a target size of 0.5 mm to 2.5 mm+/−10% and not to exceed 2.8 mm.

The manufacturing processes for the NAC drug products are filling of capsules to the desired weights containing 300 mg NAC. No additional excipients or fillers are added. There are 2 NAC manufactured dosage forms prepared for comparison: 300 mg NAC Capsules, and 300 mg Enteric NAC capsules. In the case of the enteric capsules, once the capsules are filled they are banded and then enteric coated. The banding solution composition is provided in Table 1 and the enteric coating solution composition is provided in Table 2.

TABLE 1

Banding Solution Composition

| Ingredient | % w/w |
|---|---|
| Pharmacoat 606, USP Hypromellose | 16.0% |
| FD&C Blue 1 Dye (Solution) | 0.5% |
| DI Water | 28.5% |
| Dehydrated Alcohol, 200 Proof, USP | 55.0% |
| Total | 100% |

TABLE 2

Enteric Coating Solution Composition

| Ingredient | % w/w |
|---|---|
| EUDRAGIT L 30 D-55 | 57.87% |
| Triethyl Citrate POC/NF | 0.90% |
| PlasACRYL 120 | 8.65% |
| Purified Water, USP | 32.58% |
| Total | 100% |

In some embodiments, the modified release dosage form comprises NAC and optionally one or more excipients in a capsule. The capsule seam may be coated by a band. The capsule may be enterically coated. Exemplary compositions for the band and coating solutions are as follows (the volatile components (e.g., water, alcohol) may be evaporated after application, and not found in the final coating composition):

Banding Solution Composition

| Ingredient | % w/w | % w/w range (approx..) |
|---|---|---|
| Pharmacoat 606, USP Hypromellose | 16.0% | 10-25 |
| FD&C Blue 1 Dye (Solution) | 0.5% | 0-2 |
| DI Water | 28.5% | 0-50 |
| Dehydrated Alcohol, 200 Proof, USP | 55.0% | 0-50 |

| Enteric Coating Solution Composition | | |
|---|---|---|
| Ingredient | % w/w | % w/w range (approx..) |
| EUDRAGIT L 30 D-55 | 57.87% | 40-80 |
| Triethyl Citrate POC/NF | 0.90% | 0-5 |
| PlasACRYL 120 | 8.65% | 0-20 |
| Purified Water, USP | 32.58% | 0-60 |

Pharmacokinetic Parameters

The modified release dosage forms of the present disclosure provide a systemic exposure of NAC or a salt or metabolite thereof that is significantly increased as compared to a similar immediate release dosage form of NAC, as determined, e.g., by AUC values.

In some embodiments, the relative bioavailability of NAC measured by relative AUC values of an immediate release capsule containing an amount of NAC is approximately 40, 45, 50, 55, 60, or 65% that of a coated capsule embodied herein containing the same amount of NAC.

In some embodiments, the relative bioavailability of 2,4-DSPBN measured by relative AUC values of an immediate release capsule containing an amount of 2,4-DSPBN is approximately 5, 10, 15, 20, 25, 30, 35, or 40% that of a coated capsule embodied herein containing the same amount of 2,4-DSPBN.

Accordingly, some embodiments, include methods of increasing the relative bioavailability of the first compound and/or the second compound in subject in need thereof comprising administering a modified release dosage form of the present embodiments to the subject. Other embodiments include a method of increasing the half-life of 2,4-DSPBN in subject in need thereof comprising administering a modified release dosage form of the present embodiments to the subject. In some embodiments, the administration is once daily, twice daily (b.i.d) or three times daily (t.i.d).

Methods of Use

The modified release dosage form of the present disclosure may be used, for example, in a method of treating acute acoustic trauma sensory neural hearing loss, tinnitus, vertigo, or endolympahtic hydrops, Meniere's disease, ototoxin induced hearing loss e.g. aminoglycoside, carboplatin, or cisplatin induced hearing loss ototoxin-induced injury, acetaminophen (Tylenol) poisoning, collapse of part or all of a lung (atelectasis), chest pain (angina), bipolar disorder, Air passage swelling (bronchitis), chronic obstructive pulmonary disease (COPD), fibrosing alveolitis, diagnostic lung tests, carboplatin, or cisplatin induced hearing or stroke in a subject in need thereof comprising administering a modified release dosage form of the present embodiments to the subject. Treatments may be performed in the same or similar manner to those described in US Pub. No. 20120172435.

In some embodiments, modified release dosage form of the present disclosure is administered to a human patient suffering from a central nervous system (CNS) disease. Examples of the CNS disease include congenital disorder, traumatic brain injury (e.g., closed head trauma, penetrating head trauma, blast-induced head trauma, concussion), inflammatory disease, infectious disease (e.g., meningitis, cerebritis/encephalitis, brain abscess), neoplastic disease (e.g., CNS malignancies), neurodegenerative disease (e.g., Alzheimer's Disease, Parkinson's Disease, multiple sclerosis (MS), amyotrophic lateral sclerosis (ALS), stroke associated neurodegeneration), vascular disease (e.g., ischemic stroke, hemorrhagic stroke), seizure disorders (e.g., epilepsy), and neuropsychiatric disease (e.g., depression, bipolar disorder, schizophrenia), migraine, and attention deficit/hyperactivity disorder (ADHD). Other embodiments, modified release dosage form of the present disclosure is administered to a human patient suffering from renal disease following exposure to nephrotoxic agents or treatment with nephrotoxic drugs, e.g. cisplatin, or suffering from liver diseases following exposure to hepatotoxic agents or treatment with hepatotoxic drugs, e.g. acetaminophen.

Definitions

As used herein, the singular terms "a," "an," and "the" include plural referents unless the context clearly dictates otherwise. Thus, for example, reference to a compound can include multiple compounds unless the context clearly dictates otherwise.

As used herein, the terms "substantially," "substantial," and "about" are used to describe and account for small variations. When used in conjunction with an event or circumstance, the terms can refer to instances in which the event or circumstance occurs precisely as well as instances in which the event or circumstance occurs to a close approximation. For example, the terms can refer to less than or equal to ±10%, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations, which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scopes of this invention.

Working Examples

Pharmaceutical Composition

A two part capsule was filled with NAC and/or 2,4-DSPBN. The capsule seam was the coated by a band and the entire banded capsule was enterically coated. The compositions used for the band and enteric coating were as follows: compositions for the band and coating solutions are as follows (the volatile components (e.g., water, alcohol) were evaporated after application, and not found in the final coating composition):

| Banding Solution Composition | |
|---|---|
| Ingredient | % w/w |
| Pharmacoat 606, USP Hypromellose | 16.0% |
| FD&C Blue 1 Dye (Solution) | 0.5% |
| DI Water | 28.5% |
| Dehydrated Alcohol, 200 Proof, USP | 55.0% |

| Enteric Coating Solution Composition | |
|---|---|
| Ingredient | % w/w |
| EUDRAGIT L 30 D-55 | 57.87% |
| Triethyl Citrate POC/NF | 0.90% |
| PlasACRYL 120 | 8.65% |
| Purified Water, USP | 32.58% |

Pharmacokinetic Results for Cohort 1

Figure 1:
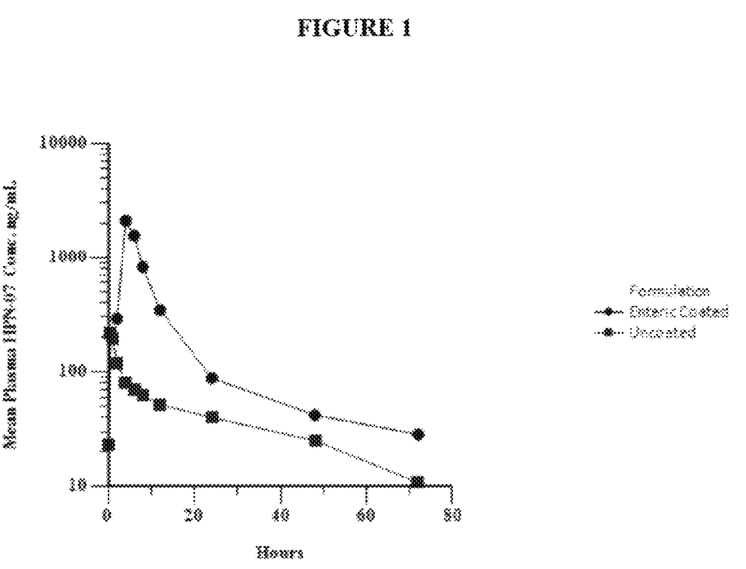
FIG. 1 shows mean 2,4-DSPBN plasma concentration versus time curves for an embodiment of the disclosure.

Disodium 2,4-disulfophenyl-N-tert-butyl nitrone ("2,4-DSPBN") exposure was greater when administered in the enteric-coated capsules compared to uncoated capsules. The $AUC_{0-\infty}$ was approximately 7-fold higher (16,700 versus 2,310 h ng/mL), and the Cmax was nearly 10-fold higher (2410 versus 244 ng/mL). Following administration of enteric-coated capsules, peak concentrations were observed later compared with uncoated capsules. The median $T_{max}$ was 5 h following administration of the enteric-coated capsules compared to 0.7 h following administration of uncoated capsules. The mean 2,4-DSPBN plasma concentration versus time curves are shown in FIG. 1 and PK parameters for 2,4-DSPBN are summarized in Table 3.

TABLE 3

Pharmacokinetic Parameters for 2,4-DSPBN Following Oral Administration of 2,4-DSPBN 1000 mg + NAC 1200 mg as Enteric-Coated or Uncoated Capsules

| PK Parameter Statistic | Enteric-Coated | | | Uncoated | | |
|---|---|---|---|---|---|---|
| | Day 1 N = 5 | Day 7 N = 5 | Combined N = 10 | Day 1 N = 5 | Day 7 N = 5 | Combined N = 10 |
| $C_{max}$ (ng/mL) | | | | | | |
| Mean | 2370 | 2440 | 2410 | 357 | 130 | 244 |
| SD | 1730 | 1060 | 1350 | 144 | 100 | 167 |
| Median | 1660 | 2450 | 2300 | 302 | 128 | 235 |
| $T_{max}$ (h) | | | | | | |
| Mean | 4.8 | 5.2 | 5.0 | 0.7 | 3.8 | 2.3 |
| SD | 1.1 | 1.1 | 1.1 | 0.3 | 3.3 | 2.8 |
| Median | 4 | 6.0 | 5.0 | 0.5 | 4.0 | 0.8 |
| $AUC_{last}{}^a$ (h · ng/mL) | | | | | | |
| Mean | 16400 | 15600 | 16000 | 1630 | 2520 | 2080 |
| SD | 6350 | 5100 | 5450 | 741 | 2470 | 1780 |
| Median | 15200 | 17000 | 16900 | 1430 | 1770 | 1490 |
| $AUC_{0-\infty}$ (hr · ng/mL) | | | | | | |
| Mean | 17400 | 16000 | 16700 | 1850 | 2780 | 2310 |
| SD | 7020 | 5230 | 5890 | 817 | 2540 | 1840 |
| Median | 16700 | 17400 | 17300 | 1710 | 2020 | 1800 |
| $t_{1/2}$ (hr) | | | | | | |
| Mean | 20.9 | 9.1 | 15.0 | 12.4 | 15.8 | 14.1 |
| SD | 13.4 | 7.52 | 12.0 | 14.1 | 4.96 | 10.2 |
| Median | 13.3 | 5.1 | 11.9 | 7.8 | 14.4 | 11.6 |
| Vz/F (mL) | | | | | | |
| Mean | 1780000 | 841000 | 1310000 | 9690000 | 18500000 | 14100000 |
| SD | 857000 | 587000 | 852000 | 10600000 | 15100000 | 13200000 |
| Median | 2060000 | 836000 | 1100000 | 4590000 | 13100000 | 7810000 |
| CL/F (mL/hr) | | | | | | |
| Mean | 67100 | 72700 | 69900 | 614000 | 939000 | 776000 |
| SD | 32900 | 39200 | 34300 | 217000 | 911000 | 647000 |
| Median | 59900 | 57400 | 57900 | 583000 | 494000 | 555000 |

TABLE 3-continued

Pharmacokinetic Parameters for 2,4-DSPBN Following Oral Administration of 2,4-DSPBN 1000 mg + NAC 1200 mg as Enteric-Coated or Uncoated Capsules

| PK Parameter Statistic | Enteric-Coated | | | Uncoated | | |
|---|---|---|---|---|---|---|
| | Day 1 N = 5 | Day 7 N = 5 | Combined N = 10 | Day 1 N = 5 | Day 7 N = 5 | Combined N = 10 |
| | $MTT^b$ (mL) | | | | | |
| Mean | 12.2 | 8.87 | 10.5 | 8.07 | 16.3 | 12.2 |
| SD | 2.0 | 2.2 | 2.7 | 6.4 | 7.6 | 7.9 |
| Median | 11.5 | 8.74 | 10.5 | 6.91 | 14.6 | 9.51 |

Figure 2:
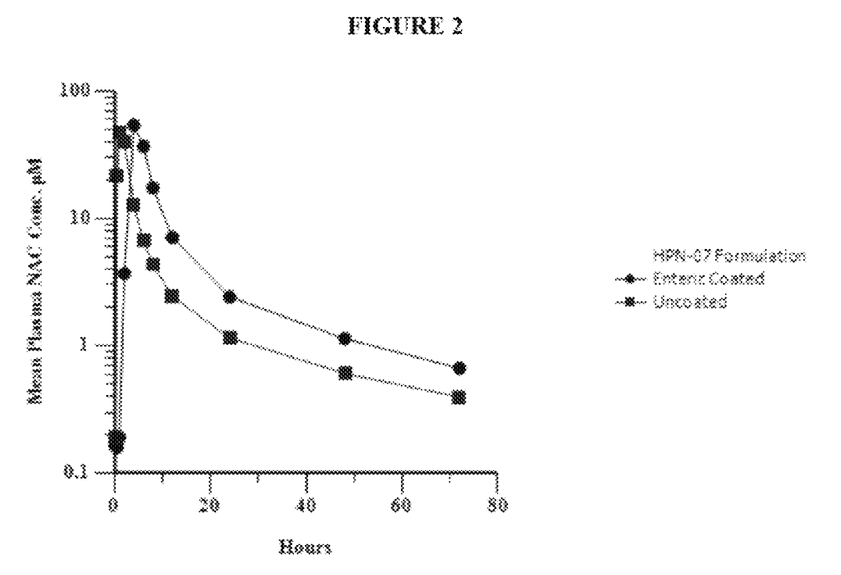
FIG. 2 shows mean NAC plasma concentration versus time curves for an embodiment of the disclosure.

Abbreviations: $AUC_{0-\infty}$ = area under the plasma concentration versus time curve from time 0 to infinity; $AUC_{last}$ = area under the plasma concentration versus time curve until the last measurable time point; $C_{max}$ = maximum observed plasma concentration; CL/F = clearance divided by the fraction of dose absorbed; MTT = mean transit time; MRT = mean residence time; NAC = N-acetylcysteine; SD = standard deviation; $t_{1/2}$ = half-life; $T_{max}$ = time to reach maximum plasma concentration; Vz/F = apparent volume of distribution divided by the fraction of dose absorbed.
[a] $AUC_{0-12\,h}$, $AUC_{0-24\,h}$, $AUC_{0-48\,h}$ or $AUC_{0-72\,h}$
[b] $MRT_{oral}$ = MTT = AUMC/AUC NAC exposure was also higher when administered as enteric-coated capsules in combination with 2,4-DSPBN in enteric-coated capsules, although the magnitude of the difference was less than that observed for 2,4-DSPBN. Mean NAC plasma concentration versus time curves are shown in FIG. 2. Following oral administration in combination with 2,4-DSPBN in enteric-coated or uncoated capsules, the NAC $AUC_{0-\infty}$ was 401 h-μmol/L and 235 h-μmol/L, respectively. A similar difference was seen in $C_{max}$, with results of 67.8 μM for enteric-coated capsules versus 48.7 μM for uncoated capsules. The NAC peak was also observed after a longer duration when 2,4-DSPBN was administered in enteric-coated capsules (median $T_{max}$ of 4.0 h versus 1.0 h). PK parameters for NAC are summarized in Table 4.

TABLE 04

Pharmacokinetic Parameters for NAC Following Oral Administration of 2,4-DSPBN 1000 mg + NAC 1200 mg as Enteric-Coated or Uncoated Capsules

| PK Parameter Statistic | Enteric-Coated | | | Uncoated | | |
|---|---|---|---|---|---|---|
| | Day 1 N = 5 | Day 7 N = 5 | Combined N = 10 | Day 1 N = 5 | Day 7 N = 5 | Combined N = 10 |
| | $C_{max}$ (ng/mL) | | | | | |
| Mean | 76.8 | 58.7 | 67.8 | 56.2 | 41.3 | 48.7 |
| SD | 33.6 | 32.5 | 32.6 | 46.9 | 8.5 | 32.7 |
| Median | 60.3 | 64.6 | 62.5 | 33.3 | 41.9 | 37.7 |
| | $T_{max}$ (h) | | | | | |
| Mean | 4.4 | 5.2 | 4.8 | 1.0 | 1.2 | 1.1 |
| SD | 0.9 | 1.1 | 1 | 0 | 0.5 | 0.3 |
| Median | 4.0 | 6.0 | 4 | 1.0 | 1.0 | 1.0 |
| | $AUC_{last}^a$ (h · ng/mL) | | | | | |
| Mean | 437 | 315 | 376 | 262 | 173 | 217 |
| SD | 109 | 121 | 126 | 183 | 17.3 | 131 |
| Median | 409 | 338 | 355 | 189 | 181 | 183 |
| | $AUC_{0-\infty}$ (hr · ng/mL) | | | | | |
| Mean | 463 | 339 | 401 | 281 | 189 | 235 |
| SD | 113 | 127 | 131 | 187 | 18.1 | 134 |
| Median | 431 | 362 | 380 | 213 | 198 | 201 |
| | $t_{1/2}$ (hr) | | | | | |
| Mean | 24.9 | 27.8 | 26.4 | 32.2 | 32.2 | 32.2 |
| SD | 2.2 | 1.6 | 2.4 | 4.6 | 1.0 | 3.1 |
| Median | 25.8 | 26.9 | 26.5 | 34.4 | 32.8 | 32.8 |

TABLE 04-continued

Pharmacokinetic Parameters for NAC Following Oral Administration of 2,4-DSPBN 1000 mg + NAC 1200 mg as Enteric-Coated or Uncoated Capsules

| PK Parameter Statistic | Enteric-Coated | | | Uncoated | | |
|---|---|---|---|---|---|---|
| | Day 1 N = 5 | Day 7 N = 5 | Combined N = 10 | Day 1 N = 5 | Day 7 N = 5 | Combined N = 10 |
| | Vz/F (mL) | | | | | |
| Mean | 595 | 980 | 787 | 1760 | 1820 | 1790 |
| SD | 135 | 382 | 338 | 1230 | 220 | 831 |
| Median | 587 | 868 | 714 | 1750 | 1760 | 1760 |
| | CL/F (mL/hr) | | | | | |
| Mean | 16.6 | 24.3 | 20.4 | 35.8 | 39.1 | 37.5 |
| SD | 3.6 | 8.9 | 7.6 | 21.5 | 3.9 | 14.7 |
| Median | 17.1 | 20.3 | 19.4 | 34.6 | 37.1 | 36.6 |
| | $MTT^b$ (mL) | | | | | |
| Mean | 13 | 13.9 | 13.4 | 10.5 | 11.1 | 10.8 |
| SD | 1.5 | 1.4 | 1.5 | 1.9 | 0.6 | 1.4 |
| Median | 13.5 | 13.8 | 13.6 | 10.9 | 11.4 | 11.1 |

Abbreviations: $AUC_{0-\infty}$ = area under the plasma concentration versus time curve from time 0 to infinity; $AUC_{last}$ = area under the plasma concentration versus time curve until the last measurable time point; $C_{max}$ = maximum observed plasma concentration; CL/F = clearance divided by the fraction of dose absorbed; MTT = mean transit time; MRT = mean residence time; NAC = N-acetylcysteine; SD = standard deviation; $t_{1/2}$ = half-life; $T_{max}$ = time to reach maximum plasma concentration; Vz/F = apparent volume of distribution divided by the fraction of dose absorbed.
[a] $AUC_{0-12\,h}$, $AUC_{0-24\,h}$, $AUC_{0-48\,h}$, or $AUC_{0-72\,h}$
[b] $MRT_{oral}$ = MTT = AUMC/AUC NAC dissolution profiles were measured according to the following procedure: Dissolution was measured using a USP II, Paddle apparatus, with 0.1 M HCl media at 37+/−0.5° C. and 75 RPM. Samples were collected at the indicated times and NAC concentrations determined by HPLC.

Figure 3:
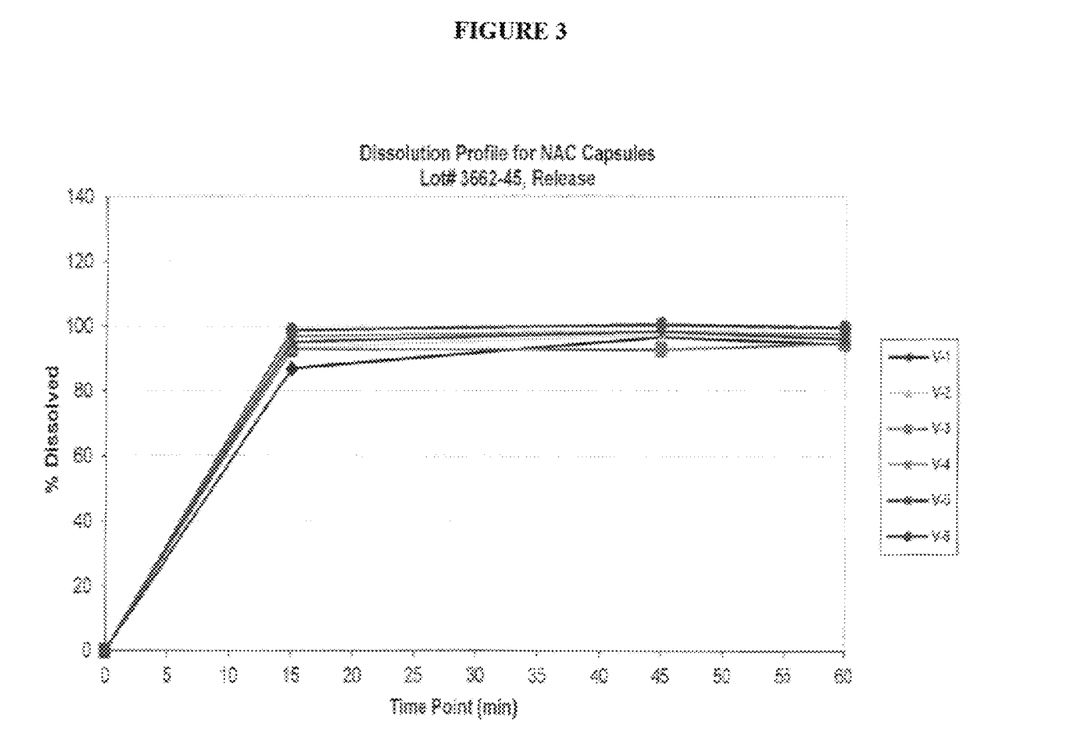
FIG. 3 shows NAC uncoated capsule dissolution profiles for an embodiment of the disclosure.

Table 5 shows the dissolution results, and FIG. 3 shows the dissolution profile.

TABLE 5

Dissolution Profile NAC Capsules

| Vessel | 0 min | 15 min | 45 min | 60 min |
|---|---|---|---|---|
| | Concentration of Drug at Sampling Time Point | | | |
| 1 | 0 | 0.52268 | .057283 | 0.57031 |
| 2 | 0 | 0.56703 | 0.57848 | 0.58111 |
| 3 | 0 | 0.55484 | 0.56185 | 0.57100 |
| 4 | 0 | 0.57672 | 0.58764 | 0.58841 |

TABLE 5-continued

Dissolution Profile NAC Capsules

| Vessel | 0 min | 15 min | 45 min | 60 min |
|---|---|---|---|---|
| 5 | 0 | 0.57397 | 0.58458 | 0.58066 |
| 6 | 0 | 0.59406 | 0.60303 | 0.59794 |

Actual Amount of Drug (mg) Dissolved at Time Point

| 1 | 0 | 261.3 | 286.4 | 285.1 |
|---|---|---|---|---|
| 2 | 0 | 283.5 | 289.2 | 290.5 |
| 3 | 0 | 277.4 | 280.9 | 285.5 |
| 4 | 0 | 288.4 | 293.8 | 294.2 |
| 5 | 0 | 287.0 | 292.3 | 290.3 |
| 6 | 0 | 297.0 | 301.5 | 299.0 |

% dissolved at time Point (min)

| 1 | 0 | 87 | 95 | 95 |
|---|---|---|---|---|
| 2 | 0 | 95 | 96 | 97 |
| 3 | 0 | 92 | 94 | 95 |
| 4 | 0 | 96 | 98 | 98 |
| 5 | 0 | 96 | 97 | 97 |
| 6 | 0 | 99 | 101 | 100 |
|  | 0 | 94 | 97 | 97 |
| Mead |  | 4.1 | 2.3 | 1.8 |
| SD |  | 4.3 | 2.3 | 1.8 |
| % RSD |  |  |  |  |

NAC dissolution profiles were measured according to the following procedure: Dissolution was measured in two stages using a USP II, Paddle apparatus, with media at 37+/−0.5° C. and 75 RPM. Stage 1 media was 0.1 M HCl for 2 hr. At 2 hr a sufficient amount 0.05 M Phosphate buffer was added to bring the pH to 6.8. Samples were collected at the indicated times and NAC concentrations determined by HPLC.

Figure 4:
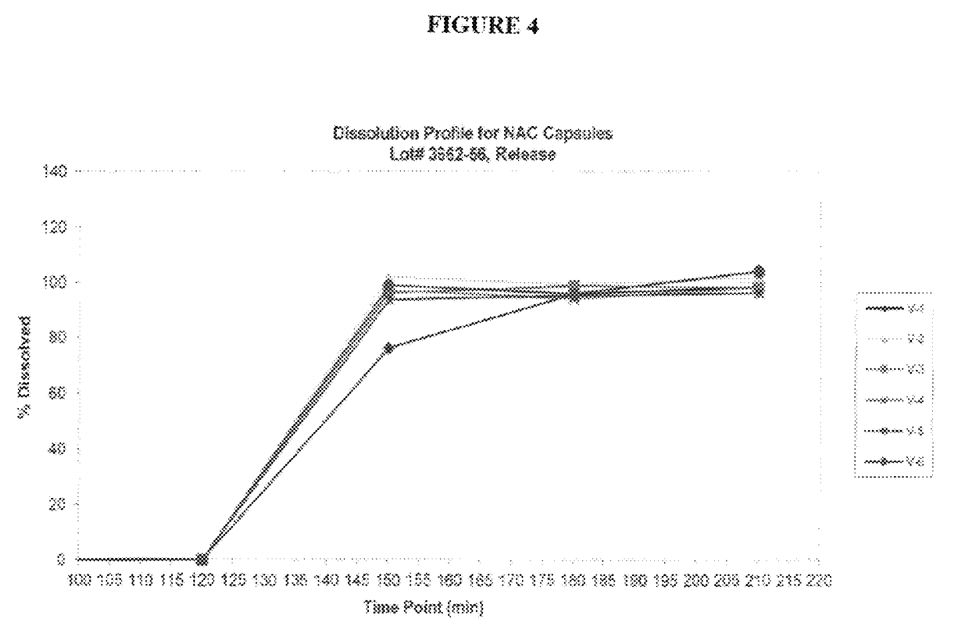
FIG. 4 shows NAC enteric coated capsule dissolution profiles for an embodiment of the disclosure.

Table 6 shows the dissolution results, and FIG. 4 shows the dissolution profile.

TABLE 6

Dissolution Profile NAC Capsules

Concentration of Drug at Sampling Time Point

| Vessel | 0 min | 120 min | 180 min | 210 min |
|---|---|---|---|---|
| 1 | 0 | 0 | 0.22877 | 0.29550 |
| 2 | 0 | 0 | 0.30615 | 0.30584 |
| 3 | 0 | 0 | 0.28885 | 0.29436 |
| 4 | 0 | 0 | 0.29127 | 0.29430 |
| 5 | 0 | 0 | 0.28159 | 0.28884 |
| 6 | 0 | 0 | 0.28817 | 0.31226 |

Actual amount of Drug (mg) Dissolved at Time Point

| Vessel | 0 min | 120 min | 150 min | 180 min | 210 min | Caplet wt (mg) |
|---|---|---|---|---|---|---|
| 1 | 0 | 0 | 228.5 | 287.4 | 295.1 | 400.34 |
| 2 | 0 | 0 | 305.8 | 297.9 | 305.5 | 416.26 |
| 3 | 0 | 0 | 288.6 | 296.4 | 294.1 | 404.91 |
| 4 | 0 | 0 | 291.0 | 282.7 | 294.0 | 410.00 |
| 5 | 0 | 0 | 281.3 | 285.8 | 288.5 | 408.19 |
| 6 | 0 | 0 | 296.7 | 287.9 | 311.9 | 410.26 |

% dissolved at time Point (min)

| Vessel | 0 min | 120 min | 150 min | 180 min | 210 min |
|---|---|---|---|---|---|
| 1 | 0 | 0 | 76 | 96 | 98 |
| 2 | 0 | 0 | 102 | 99 | 102 |
| 3 | 0 | 0 | 96 | 99 | 98 |
| 4 | 0 | 0 | 97 | 94 | 98 |

TABLE 6-continued

Dissolution Profile NAC Capsules

| 5 | 0 | 0 | 94 | 95 | 96 |
|---|---|---|---|---|---|
| 6 | 0 | 0 | 99 | 96 | 104 |
| Mean | 0 | 0 | 94 | 97 | 99 |
| SD |  |  | 9.1 | 2.0 | 2.9 |
| % RSD |  |  | 9.7 | 2.1 | 2.9 |

What is claimed is:

1. A modified release dosage form, comprising
(a) a first compound that is N-acetylcysteine or a salt thereof;
(b) optionally, a second compound that is a pharmaceutically acceptable compound capable of forming a radical adduct; and
(c) a coating layer encapsulating the first compound, wherein the coating layer solubilizes at a pH above 5.4 and below 6.7 in a physiological environment, wherein the modified release dosage form, after a single administration to a human subject in need of treatment thereof, produces in the subject a mean area under the plasma concentration versus time curve (0-inf) ($AUC_{0-inf}$) of N-acetylcysteine that is greater than that produced after a single administration of a pharmaceutical composition containing an equivalent composition of N-acetylcysteine or a salt thereof, but without a coating layer that prevents release of the first compound at a pH of less than 5.5.

2. The modified release dosage form of claim 1, wherein the second compound comprises a nitrone moiety.

3. The modified release dosage form of claim 2, wherein the second compound is 2,4-disulfophenyl-N-tert-butyl nitrone, or a salt thereof.

4. The modified release dosage form of claim 3, wherein the second compound is disodium 2,4-disulfophenyl-N-tert-butyl nitrone.

5. The modified release dosage form of claim 1, wherein the coating layer encapsulates the first compound and the second compound.

6. The modified release dosage form of claim 1, wherein the weight ratio of the N-acetylcysteine to the pharmaceutically acceptable compound capable of forming a radical adduct is from about 1:0.08 to about 1:8.

7. The modified release dosage form of claim 1, wherein the modified release dosage form is in the form of a tablet or capsule.

8. The modified release dosage form of claim 1, wherein the modified release dosage form is in the form of a capsule comprising coated pellets or beads.

9. The modified release dosage form of claim 1, wherein the modified release dosage form is a pharmaceutical composition suitable for oral administration.

10. A modified release pharmaceutical composition, comprising
pellets or beads comprising a first compound that is N-acetylcysteine or a salt thereof, and
optionally, a second compound that is a pharmaceutically acceptable compound capable of forming a radical adduct,
wherein the pellets or beads comprise a core that comprises the first and a coating layer encapsulating the core that prevents release of the first compound at a pH of less than 5.5, wherein the coating layer solubilizes at a pH above 5.4 and below 6.7, wherein the modified release pharmaceutical composition, after a single administration to a human subject in need of treatment thereof, produces in the subject a mean area under the plasma concentration versus time curve (0-inf) ($AUC_{0-inf}$) of N-acetylcysteine that is greater than that produced after a single administration of a pharmaceutical composition containing an equivalent composition of N-acetylcysteine or a salt thereof, but without a coating encapsulating the core that prevents release of the first compound at a pH of less than 5.5.

11. The pharmaceutical composition of claim 10, wherein the second compound is in the form of pellets or beads, and the pellets or beads comprise a core that contains the second compound and a coating encapsulating the core that prevents release of the second compound at a pH of less than 5.5.

12. The pharmaceutical composition of claim 10, wherein the second compound is a 2,4-disulfophenyl-N-tert-butyl nitrone or a salt thereof.

13. The pharmaceutical composition of claim 10, wherein the second compound is disodium 2,4-disulfophenyl-N-tert-butyl nitrone.

14. The pharmaceutical composition of claim 11, wherein the modified release pharmaceutical composition is in the form of a capsule.

15. The pharmaceutical composition of claim 11, wherein the coating for the core comprising the first compound and the coating for the core comprising the second compound are of the same composition.

16. The pharmaceutical composition of claim 10, wherein the core comprising the first compound also comprise the second compound.

17. The pharmaceutical composition of claim 10, wherein the weight ratio of the N-acetylcysteine or a salt thereof to the pharmaceutically acceptable compound capable of forming a radical adduct is from about 1:0.08 to about 1:8.

18. The pharmaceutical composition of claim 10, wherein the coating layer provides for release of the first compound within a mammal's duodenum upon oral administration.

19. A modified release dosage form, comprising
(a) a first compound that is N-acetylcysteine or a salt thereof;
(b) optionally, a second compound that is a pharmaceutically acceptable compound capable of forming a radical adduct; and
(c) a coating layer encapsulating the first compound and/or a second compound if present,
wherein the first compound and/or the second compound, if present, are released within a mammal's duodenum.

* * * * *